United States Patent
Su et al.

(10) Patent No.: US 11,365,178 B2
(45) Date of Patent: Jun. 21, 2022

(54) METHOD FOR PREPARING ELAGOLIX INTERMEDIATE AND COMPOSITION THEREOF

(71) Applicants: ZHEJIANG HUAHAI PHARMACEUTICAL CO., LTD., Linhai (CN); SHANGHAI SYNCORES TECHNOLOGIES, INC, Shanghai (CN)

(72) Inventors: Hu Su, Shanghai (CN); Xiaowen Guo, Shanghai (CN); Yukun Liang, Shanghai (CN); Kaiqiang Shi, Shanghai (CN); Jintao Yang, Shanghai (CN); Kang He, Shanghai (CN); Anping Tao, Shanghai (CN); Luning Huang, Shanghai (CN); Jianguo An, Shanghai (CN); Xi Chen, Shanghai (CN); Hong Gu, Shanghai (CN)

(73) Assignees: ZHEJIANG HUAHAI PHARMACEUTICAL CO., LTD., Linhai (CN); SHANGHAI SYNCORES TECHNOLOGIES, INC, Shanghai (CN)

( * ) Notice: Subject to any disclaimer, the term of this patent is extended or adjusted under 35 U.S.C. 154(b) by 50 days.

(21) Appl. No.: 16/957,685

(22) PCT Filed: Dec. 25, 2018

(86) PCT No.: PCT/CN2018/123468
§ 371 (c)(1),
(2) Date: Jun. 24, 2020

(87) PCT Pub. No.: WO2019/128983
PCT Pub. Date: Jul. 4, 2019

(65) Prior Publication Data
US 2020/0369625 A1    Nov. 26, 2020

(30) Foreign Application Priority Data

Dec. 27, 2017 (CN) .......................... 201711445252.5

(51) Int. Cl.
*C07D 239/54* (2006.01)
(52) U.S. Cl.
CPC .................. *C07D 239/54* (2013.01)
(58) Field of Classification Search
CPC .................................................. C07D 239/54
See application file for complete search history.

(56) References Cited

U.S. PATENT DOCUMENTS

2007/0191403 A1  8/2007  Guo et al.
2020/0369625 A1  11/2020 Su et al.

FOREIGN PATENT DOCUMENTS

| CN | 1819829 A | 8/2006 |
|---|---|---|
| CN | 109970663 A | 7/2019 |
| WO | WO-2009062087 A1 | 5/2009 |

OTHER PUBLICATIONS

Office Action, corresponding Chinese Application No. 201880081586. 5, dated Jul. 21, 2021.

(Continued)

*Primary Examiner* — Bruck Kifle
(74) *Attorney, Agent, or Firm* — Marshall, Gerstein & Borun LLP

(57) ABSTRACT

The present invention relates to a method for preparing an intermediate (Formula IV) of sodium elagolix. The intermediate is prepared by the following route. The method has advantages of simple and safe operation, high yield, less environmental pollution, good economic effect and suitability for industrial production, wherein R represents C1-C4 substituted or unsubstituted benzyl or allyl.

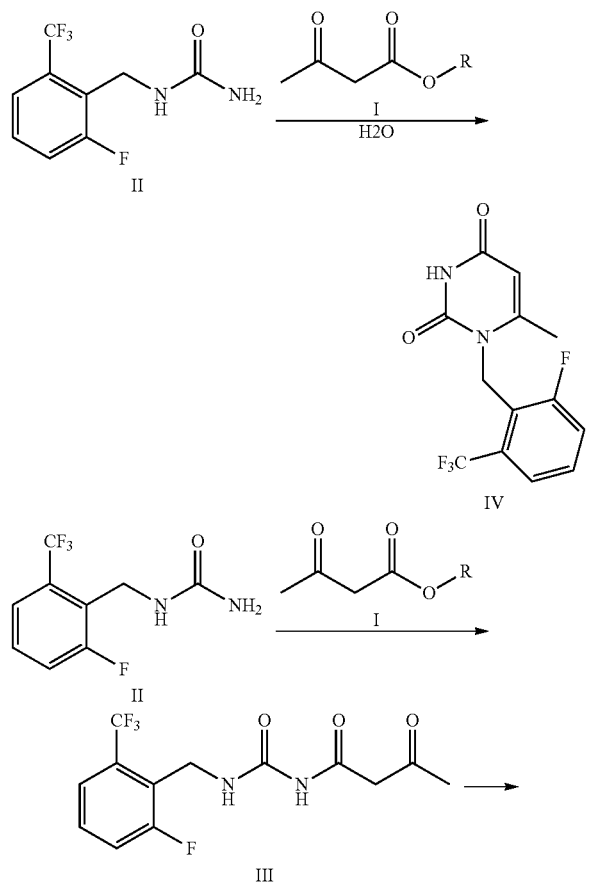

(Continued)

-continued

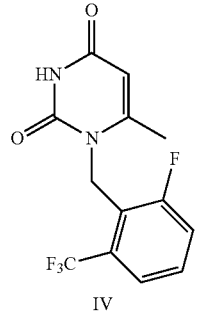

IV

16 Claims, No Drawings

(56) References Cited

OTHER PUBLICATIONS

Extended European Search Report for Application No. EP 18895688.2, dated Aug. 30, 2021.
Search Report for Chinese Application No. 2018800815865, dated Jan. 19, 2021.
Zhao et al., "5-Aryluracils as potent GnRH antagonists—Characterization of atropisomers", *Bioorganic & Medicinal Chemistry Letters*, vol. 18, pp. 3344-3349 (2008).
Office Action, corresponding Chinese Application No. 201880081586.5, dated Jan. 25, 2021.
International Search Report for Application No. PCT/CN2018/123468, dated Apr. 1, 2019. (English Translation).

METHOD FOR PREPARING ELAGOLIX INTERMEDIATE AND COMPOSITION THEREOF

TECHNICAL FIELD

The present invention belongs to the field of pharmaceutical chemistry, in particular relates to a method for preparing an intermediate of elagolix and a composition comprising the intermediate.

TECHNICAL BACKGROUND

Endometriosis is a common and frequently-occurring gynecological disease, which is a common benign infiltrative disease common to women in childbearing age and is one of the gynecological intractable diseases. The prevalence rate of middle-aged women is about 15%. The disease usually begins mostly between 30-49 years old. Women in childbearing age suffering from this disease account for 70%-80% of infertility patients, which seriously affects women's physical and mental health, work and fertility. Elagolix is an orally active non-peptide gonadotropin-releasing hormone receptor (GnRH) antagonist developed by AbbVie and Neurocrine Biosciences Inc. (NBIX) for the treatment of endometriosis. At present, the drug has submitted an application to FDA. Its structural formula is shown by Formula I:

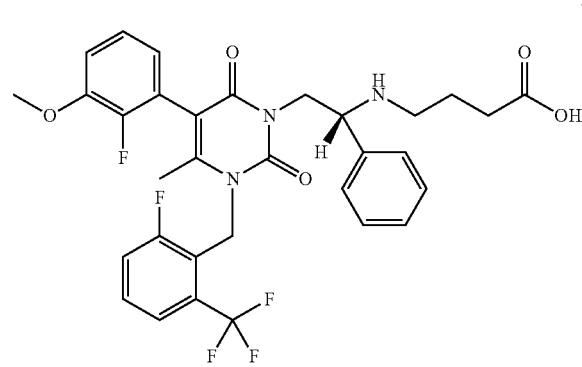

I

There are only a few reports about the compound of Formula IV as a key intermediate for preparing the elagolix.

A synthesis route reported by CN200480019502 is as follows.

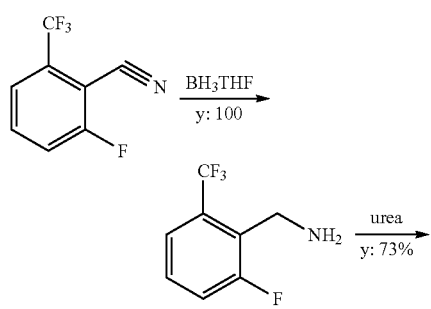

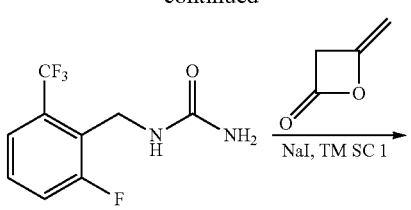

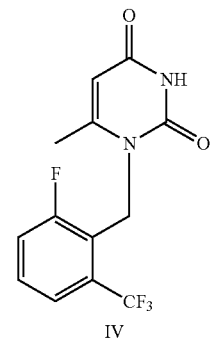

IV

The route uses toxic and explosive diketene, which has high safety risks and is not suitable for industrial production.

Another synthetic route reported in WO 2009062087 A1 is as follows.

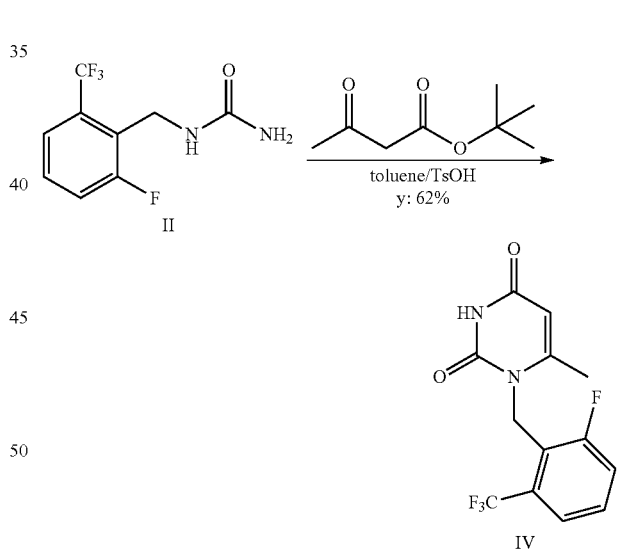

IV

The yield of this synthetic route is only 62%, and we repeated this route with a yield of only 57%. The yield of this synthetic route is relatively low, resulting in a large amount of material waste and an increase in cost. Moreover, the post-treatment needs to be stirred overnight and the process time is long, which is not suitable for industrial production. And a large amount of impurity exists along with the compound of Formula IV, which make the purification difficult.

Therefore, it is of great significance to develop a new method for preparing intermediate of elagolix.

SUMMARY OF THE INVENTION

The present invention is accomplished, in order to overcome the defects of using toxic reagents, low yield, troublesome post-treatment and the like during the process for preparing the compound of Formula IV of the intermediate of elagolix in the prior art. The present invention mainly relates to a method for preparing an intermediate of sodium elagolix, which is represented by Formula IV.

The first aspect of the present invention is to provide a method for preparing a compound of Formula IV comprising steps of: carrying out ammonolysis reaction of a compound of Formula I and a compound of Formula II in a mixed solvent of organic solvent and water, and then carrying out cyclization reaction catalyzed by acid to obtain the compound of Formula IV.

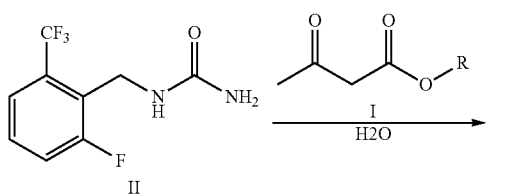

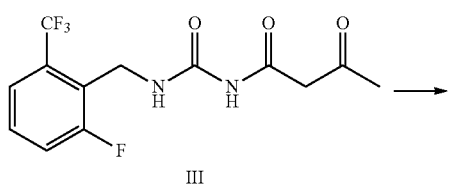

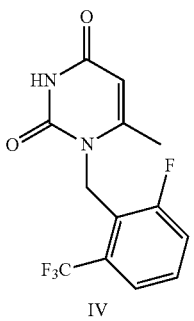

wherein R is selected from a group consisting of linear or branched $C_1$-$C_4$ substituents or benzyl.

The linear or branched $C_1$-$C_4$ substituent is alkyl or alkenyl. The alkyl is preferably methyl, ethyl, isopropyl or tert-butyl. The alkenyl group is preferably allyl.

The organic solvent is an aprotic organic solvent. Preferably, the aprotic organic solvent is one or more selected from a group consisting of toluene, chlorobenzene, xylene, N,N-dimethylformamide (DMF) and dimethyl sulfoxide (DMSO). More preferably, the organic solvent is toluene.

Specifically, the method for preparing the compound of Formula IV comprises steps of:

(1) mixing a compound of Formula I, a compound of Formula II, organic solvent and water, performing reflux reaction, stratifying the reaction system after the reaction, and keeping an organic layer;

(2) adding acid into the organic layer to continue the reaction, and performing separation and purification after the reaction to obtain the compound of Formula IV.

Preferably, the volume ratio of the organic solvent to water is 1:0.001-2; and more preferably 1:0.1-1.0.

Preferably, the mass ratio of the compound of Formula I to the compound of Formula II is 1:0.66-4, more preferably 1:1.5-2.0.

Preferably, the ratio of the mass of the compound of Formula II to the volume of the mixed solvent is 1:8 to 1:20 (g/ml).

Preferably, the reaction temperature of the ammonolysis reaction is 80° C. to 150° C., preferably 100° C. to 120° C.

Preferably, the reaction temperature of the cyclization reaction catalyzed by acid is 40° C. to 150° C., preferably 60° C. to 120° C., and the time for reaction is 0.5 h to 6 h, preferably 1 h to 3 h.

Preferably, the acid is selected from a group consisting of p-toluenesulfonic acid, methanesulfonic acid, and sodium dihydrogen phosphate; more preferably the acid is p-toluenesulfonic acid.

Preferably, the mass ratio of the compound of Formula II to the acid is 1:0.5-1.5.

Studies have found that during the process for synthesizing the compound of Formula III according to the method in WO 2009062087 A1, when toluene is used as a reaction solvent then acidification reaction is carried out, a large amount of impurities of Formula IV-imp are generated, and the polarity of the impurities is relatively similar to that of the compound of Formula IV. Several times of crystallization are needed to remove the impurities, but these impurities cannot be completely removed, which results in that the post-treatment is troublesome and available materials are wasted.

After repeated experiments, the inventors of the present invention found that the impurities of Formula III-imp produced in the reaction can be re-converted into the raw materials of Formula I and Formula II (instead of almost all of them being converted into Formula IV-imp) in the presence of water when the mixed solvent of organic solvent and water is used as the reaction solvent in the synthesis of the compound of Formula III, so that the raw materials can be further fully converted into Formulas III and IV. Thus the production of the impurities of Formula IV-imp is reduced, the utilization rate of the raw materials is improved, and the yield is obviously further improved. The reaction solvent, water and the organic solvent, is easy to be recovered, thus reducing the treatment cost of the wastes. The reaction condition is mild, and the method has the advantages of simple post-treatment, high yield, and suitability for industrialization and the like. The reaction mechanism is shown as follows:

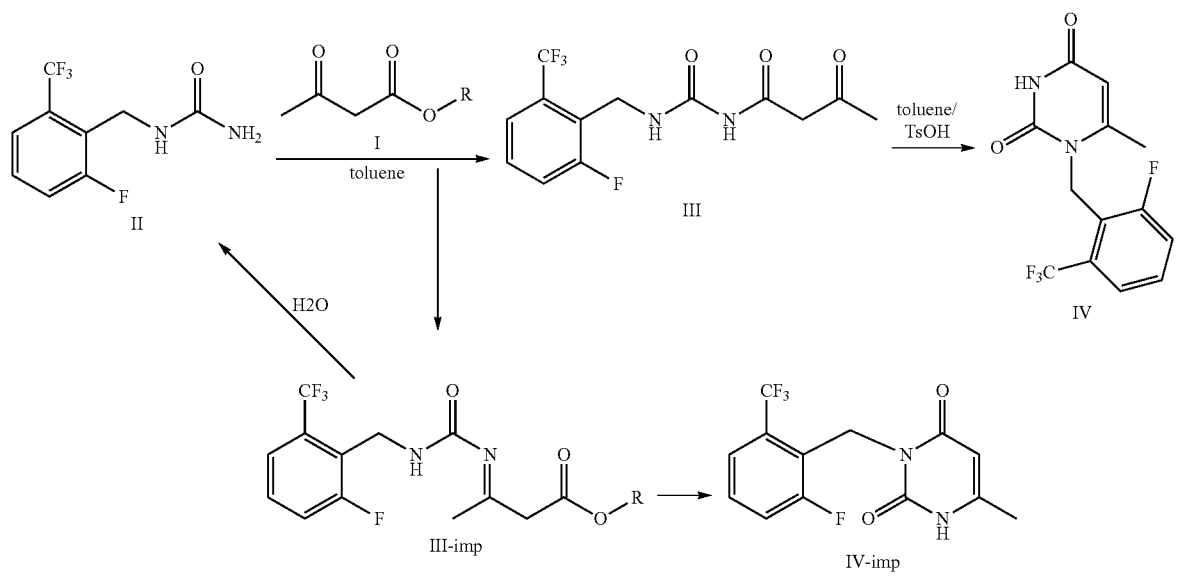

The second aspect of the present invention is to provide a composition comprising a compound of Formula IV with a content of not less than 99.5% of and a compound of Formula IV-imp with a content of not more than 0.5%, wherein the contents of both are determined by an HPLC area normalization method. The composition can be used for preparing high-purity elagolix. Preferably, the compound of Formula IV is prepared by the aforementioned method.

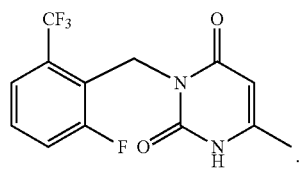

Advantageous Effect of the Technical Solution of the Present Invention

1. Compared with the prior art, the present invention avoids further generation of the impurity compound of Formula IV-imp in case that the compound of Formula III-imp is generated, thereby reducing the presence of the impurity compound of Formula IV-imp in the compound of the Formula IV. The present invention not only improves the yield, but also solves the problems that the impurity is difficult to be removed and the post-treatment is troublesome. Further, in the present invention, the operation is simple and convenient, and the manufacturing cost is reduced.

2. In the present invention, the reaction solvent, water and the organic solvent, is easy to be recovered, the reaction conditions are mild, and the method has the advantages of simple post-treatment, suitability for industrialization and the like.

EMBODIMENTS

Hereinafter, embodiments of the present invention will be described in detail with reference to examples. Embodiments of the present invention include, but are not limited to, the following examples, which should not be considered as limiting the protection scope of the present invention.

The synthesis of the raw material, a compound of Formula II can refer to the prior art CN100424078C, the entire content of which is incorporated herein by reference.

HPLC analysis conditions for measuring the content of the compound of Formula IV and the compound of Formula IV-imp are shown as follows.

Column: Waters Xbridge-Phenyl 4.6*150 mm 3.5 μm
Eluent A: 1.0 ml of perfluorobutyric acid in 1 L of water (% V/V)
Eluent B: MEOH:ACN=1:1(% V/V)
Gradient:

| Time (min) | Eluent A | Eluent B |
|---|---|---|
| 0.00 | 60 | 40 |
| 17 | 30 | 70 |
| 20 | 30 | 70 |
| 20.1 | 60 | 40 |
| 30 | 60 | 40 |

Flow rate: 1.0 mL/min
Running time: 30 min
Sample volume: 10 μL
Detector: 265 nm
Column temperature: 30° C.

EXAMPLE 1

Synthesis of 1-[2-fluoro-6-(trifluoromethyl) benzyl]-6-methylpyrimidin-2,4(1H,3H)-dione (Formula IV)

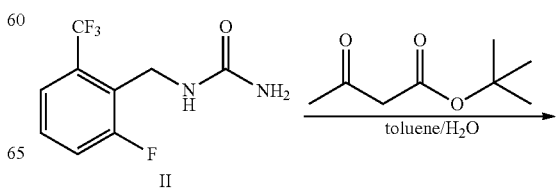

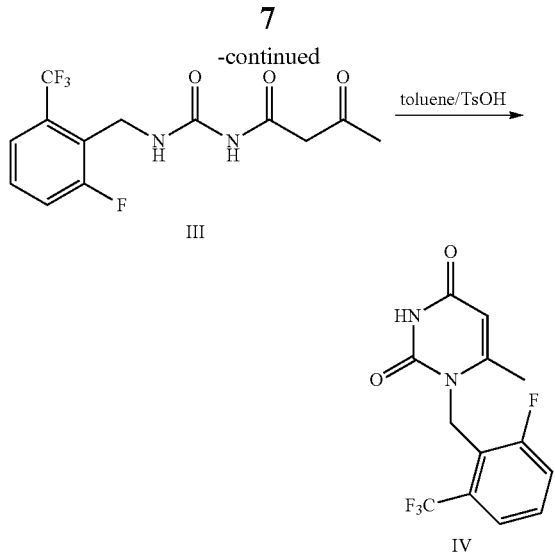

Compound of Formula II 1-[2-fluoro-6-(trifluoromethyl)] benzyl urea (100 g), tert-butyl acetoacetate (194.2 g), toluene (1000 ml) and purified water (100 ml) were added to a 2 L flask and stirred for reflux reaction for 6 h. The reaction system was stratified and the upper organic layer was retained. P-toluenesulfonic acid monohydrate (104 g) was added to the obtained organic layer, and thus obtained mixture was stirred and reacted at 60° C. for 2 h. Then, the mixture was cooled to room temperature and was stirred. Purified water (300 ml) was added thereto under stirring. The mixture was stratified, the upper organic layer was retained and concentrated, and crystallized in isopropanol to obtain 104.9 g of the compound of Formula IV with a yield of 82%. The results were shown in Table 1. $^1$H NMR (400 MHz, CDCl$_3$) δ 2.15 (s, 3H), 5.37 (s, 2H), 5.60 (s, 2H), 7.23-7.56 (m, 3H), 9.02 (s, 1H). MS(ESI) m/z 303.0([M+H]$^+$).

EXAMPLE 2

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (30 g), tert-butyl acetoacetate (58.3 g), toluene (300 ml) and purified water (50 ml) were added to a 1 L flask and stirred for reflux reaction for 6 h. The reaction system was stratified and the upper organic layer was retained. P-toluenesulfonic acid monohydrate (31.2 g) was added to the obtained organic layer, and thus obtained mixture was stirred and reacted at 60° C. for 2 h. Then, the mixture was cooled to room temperature and was stirred. Purified water (90 ml) was added thereto under stirring. The mixture was stratified, the upper organic layer was retained and concentrated, and thus obtained product was crystallized in isopropanol to obtain 31.1 g of the compound of Formula IV with a yield of 81%. MS(ESI) m/z 303.0([M+H]$^+$). The results were shown in table 1.

EXAMPLE 3

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (50 g), tert-butyl acetoacetate (94.1 g), toluene (500 ml) and purified water (500 ml) were added to a 1 L flask and stirred for reflux reaction for 6 h. The reaction system was stratified and the upper organic layer was retained. P-toluenesulfonic acid monohydrate (52 g) was added to the obtained organic layer, and thus obtained mixture was stirred and reacted at 60° C. for 2 h. Then, the mixture was cooled to room temperature and was stirred. Purified water (150 ml) was added thereto under stirring. The mixture was stratified, the upper organic layer was retained and concentrated, and thus obtained product was crystallized in isopropanol to obtain 60.9 g of the compound of Formula IV with a yield of 81%. MS(ESI) m/z 303.0 ([M+H]$^+$). The results were shown in table 1.

EXAMPLE 4

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (50 g), tert-butyl acetoacetate (94.1 g), chlorobenzene (500 ml) and purified water (100 ml) were added to a 1 L flask and stirred for reflux reaction for 6 h. The reaction system was stratified and the upper organic layer was retained. P-toluenesulfonic acid monohydrate (52 g) was added to the obtained organic layer, and thus obtained mixture was stirred and reacted at 60° C. for 2 h. Then, the mixture was cooled to room temperature and was stirred. Purified water (150 ml) was added thereto under stirring. The mixture was stratified, the upper organic layer was retained and concentrated, and thus obtained product was crystallized in isopropanol to obtain 49.9 g of the compound of Formula IV with a yield of 78%. MS(ESI) m/z 303.0 ([M+H]$^+$). The results were shown in table 1.

EXAMPLE 5

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (25 g), tert-butyl acetoacetate (47 g), xylene (250 ml) and purified water (200 ml) were added to a 1 L flask and stirred for reflux reaction for 6 h. The reaction system was stratified and the upper organic layer was retained. P-toluenesulfonic acid monohydrate (27 g) was added to the obtained organic layer, and thus obtained mixture was stirred and reacted at 60° C. for 2 h. Then, the mixture was cooled to room temperature and was stirred. Purified water (75 ml) was added thereto under stirring. The mixture was stratified, the organic layer was retained and concentrated, and thus obtained product was crystallized in isopropanol to obtain 24.6 g of the compound of Formula IV with a yield of 77%. MS(ESI) m/z 303.0([M+H]$^+$). The results were shown in table 1.

EXAMPLE 6

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (30 g), tert-butyl acetoacetate (58.3 g), N,N-dimethylformamiade (300 ml) and purified water (300 ml) were added to a 1 L flask and stirred at 120° C. to react for 4 h. The reaction system was cooled and concentrated. Toluene (300 ml), p-toluenesulfonic acid monohydrate (31 g) were added to the obtained concentrate. The mixture was stirred and reacted at 60° C. for 2 h. Then, the mixture was cooled to room temperature and was stirred. Purified water (75 ml) was added thereto under stirring. The mixture was stratified, the upper organic layer was retained and concentrated, and thus obtained product was crystallized in isopropanol to obtain 29.1 g of the compound of Formula IV with a yield of 76%. MS(ESI) m/z 303.0([M+H]$^+$). The results were shown in table 1.

EXAMPLE 7

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (30 g), tert-butyl acetoacetate (58.3 g), dimethyl sulfoxide (300 ml) and purified water (150 ml) were added to a 1 L flask and stirred at 120° C. to react for 4 h. The reaction system was cooled, and p-toluenesulfonic acid monohydrate (31 g) was added thereto and stirred. The mixture was reacted at 60° C. for 2 h. Then, the mixture was cooled to room temperature and was stirred. Purified water (150 ml) was added thereto, and the obtained mixture was extracted with ethyl acetate. The organic layer was washed with saline, dried over anhydrous sodium sulfate and filtered. The filtrate was concentrated, and thus obtained product was crystallized in isopropanol to obtain 29.6 g of the compound of Formula IV with a yield of 77%. MS(ESI) m/z 303.0([M+H]$^+$). The results were shown in table 1.

EXAMPLE 8

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (25 g), tert-butyl acetoacetate (47 g), toluene (250 ml) and purified water (150 ml) were added to a 1 L flask and stirred for reflux reaction for 6 h. The reaction system was stratified and the upper organic layer was retained. P-toluenesulfonic acid monohydrate (27 g) was added to the obtained organic layer, and thus obtained mixture was stirred and reacted at 60° C. for 2 h. Then, the mixture was cooled to room temperature and was stirred. Purified water (75 ml) was added thereto under stirring. The mixture was stratified, the upper organic layer was retained and concentrated, and thus obtained product was recrystallized in isopropanol to obtain 31.1 g of the compound of Formula IV with a yield of 81%. MS(ESI) m/z 303.0([M+H]$^+$). The results were shown in table 1.

EXAMPLE 9

Synthesis of 1-[2-fluoro-6-(trifluoromethyl) benzyl]-6-methylpyrimidin-2,4(1H,3H)-dione (Formula IV)

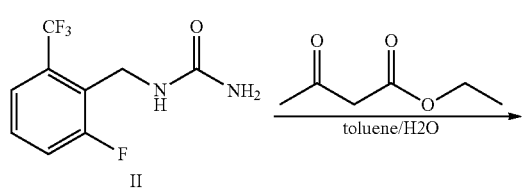

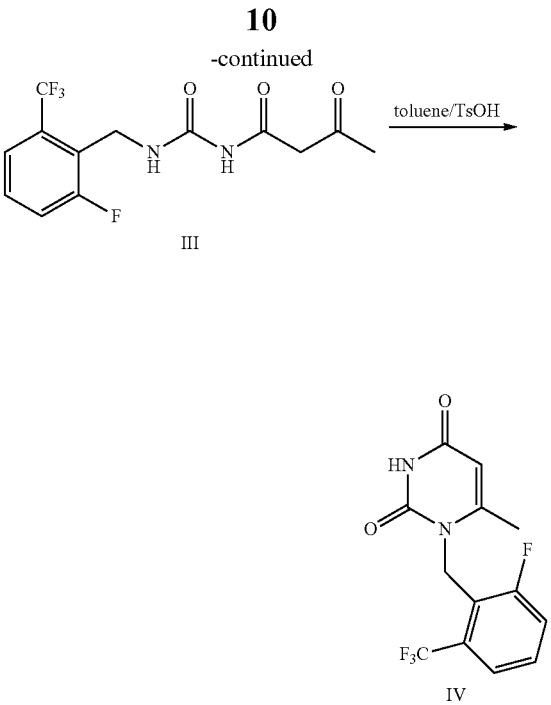

Compound of Formula II 1-[2-fluoro-6-(trifluoromethyl)] benzyl urea (50 g), ethyl acetoacetate (63.9 g), toluene (500 ml) and purified water (200 ml) were added to a 1 L flask and stirred for reflux reaction for 6 h. The reaction system was stratified and the upper organic layer was retained. P-toluenesulfonic acid monohydrate (52 g) was added to the obtained organic layer, and thus obtained mixture was stirred and reacted at 60° C. for 2 h. Then, the mixture was cooled to room temperature and was stirred. Purified water (150 ml) was added thereto under stirring. The mixture was stratified, the upper organic layer was retained and concentrated, and thus obtained product was crystallized in isopropanol to obtain 48.5 g of the compound of Formula IV with a yield of 77%. MS(ESI) m/z 303.0([M+H]$^+$). The results were shown in table 1.

EXAMPLE 10

Synthesis of 1-[2-fluoro-6-(trifluoromethyl) benzyl]-6-methylpyrimidin-2,4(1H,3H)-dione (Formula IV)

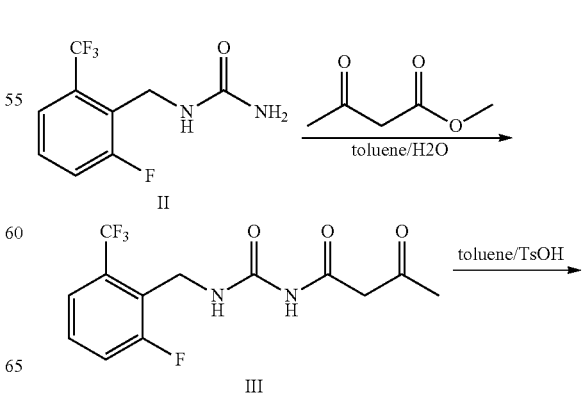

-continued

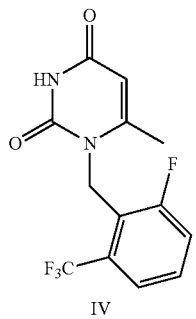

Compound of Formula II 1-[2-fluoro-6-(trifluoromethyl)] benzyl urea (50 g), methyl acetoacetate (71.3 g), toluene (500 ml) and purified water (150 ml) were added to a 1 L flask and stirred for reflux reaction for 6 h. The reaction system was stratified and the upper organic layer was retained. P-toluenesulfonic acid monohydrate (52 g) was added to the obtained organic layer, and thus obtained mixture was stirred and reacted at 60° C. for 2 h. Then, the mixture was cooled to room temperature and was stirred. Purified water (150 ml) was added thereto under stirring. The mixture was stratified, the upper organic layer was retained and concentrated, and thus obtained product was crystallized in isopropanol to obtain 49.0 g of the compound of Formula IV with a yield of 78%. MS(ESI) m/z 303.0 ([M+H]$^+$). The results were shown in table 1.

EXAMPLE 11

Synthesis of 1-[2-fluoro-6-(trifluoromethyl) benzyl]-6-methylpyrimidin-2,4(1H,3H)-dione (Formula IV)

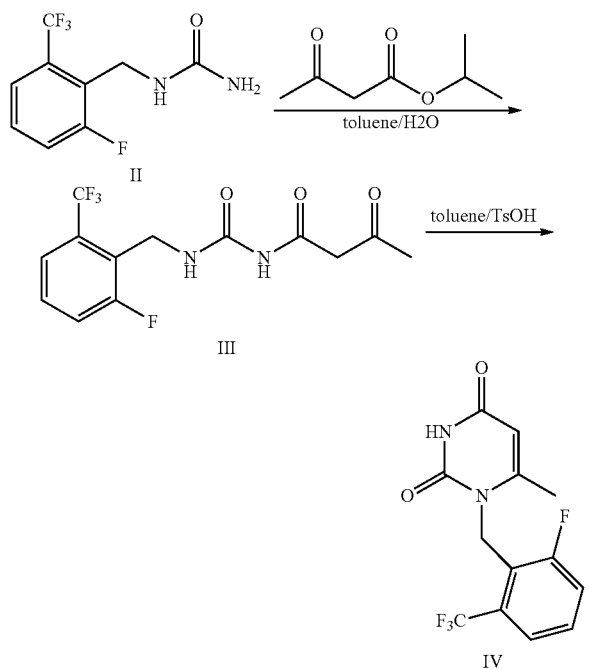

Compound of Formula II 1-[2-fluoro-6-(trifluoromethyl)] benzyl urea (50 g), isopropyl acetoacetate (88.5 g), toluene (500 ml) and purified water (4.5 g) were added to a 1 L flask and stirred for reflux reaction for 6 h. The reaction system was stratified and the upper organic layer was retained. P-toluenesulfonic acid monohydrate (52 g) was added to the obtained organic layer, and thus obtained mixture was stirred and reacted at 60° C. for 2 h. Then, the mixture was cooled to room temperature and was stirred. Purified water (150 ml) was added thereto under stirring. The mixture was stratified, the upper organic layer was retained and concentrated, and thus obtained product was crystallized in isopropanol to obtain 49.2 g of the compound of Formula IV with a yield of 77%. MS(ESI) m/z 303.0([M+H]$^+$). The results were shown in table 1.

EXAMPLE 12

Synthesis of 1-[2-fluoro-6-(trifluoromethyl) benzyl]-6-methylpyrimidin-2,4(1H,3H)-dione (Formula IV)

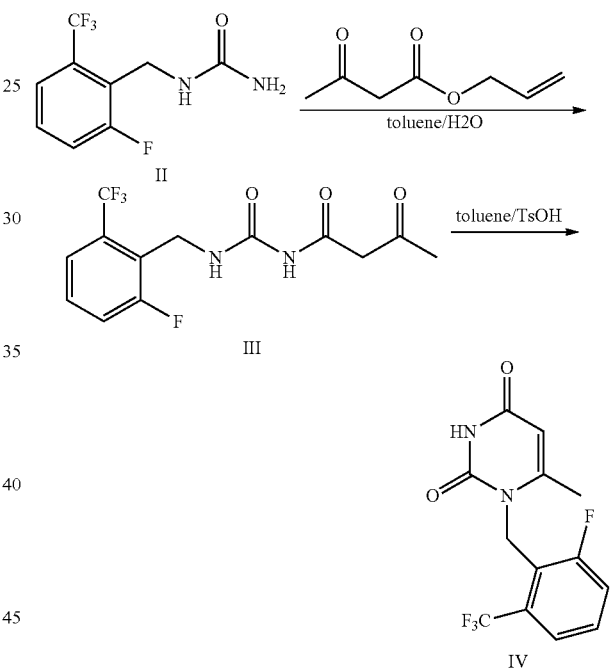

Compound of Formula II 1-[2-fluoro-6-(trifluoromethyl)] benzyl urea (30 g), allyl acetoacetate (52.4 g), toluene (300 ml) and purified water (150 ml) were added to a 1 L flask and stirred at 120° C. to react for 4 h. The reaction system was cooled, and p-toluenesulfonic acid monohydrate (31 g) was added thereto and stirred. The mixture was reacted at 60° C. for 2 h. Then, the mixture was cooled to room temperature and was stirred. Purified water (150 ml) was added thereto, and the obtained mixture was extracted with ethyl acetate. The organic layer was washed with saline, dried over anhydrous sodium sulfate and filtered. The filtrate was concentrated, and thus obtained product was crystallized in isopropanol to obtain 29.1 g of the compound of Formula IV with a yield of 76%. MS(ESI) m/z 303.0([M+H]$^+$). The results were shown in table 1.

EXAMPLE 13

Synthesis of 1-[2-fluoro-6-(trifluoromethyl) benzyl]-6-methylpyrimidin-2,4(1H,3H)-dione (Formula IV)

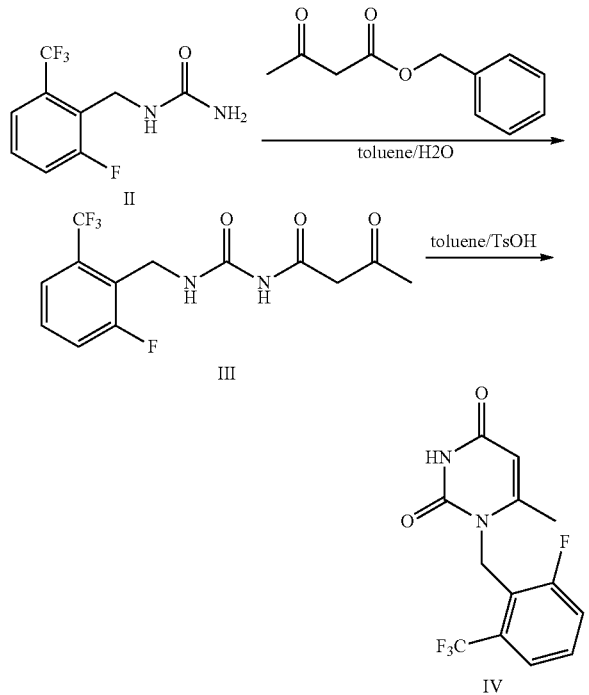

Compound of Formula II 1-[2-fluoro-6-(trifluoromethyl)] benzyl urea (50 g), benzyl acetoacetate (118 g), toluene (500 ml) and purified water (4.5 g) were added to a 1 L flask and stirred for reflux reaction for 6 h. The reaction system was stratified and the upper organic layer was retained. P-toluenesulfonic acid monohydrate (52 g) was added to the obtained organic layer, and thus obtained mixture was stirred and reacted at 60° C. for 2 h. Then, the mixture was cooled to room temperature and was stirred. Purified water (150 ml) was added thereto under stirring. The mixture was stratified, the upper organic layer was retained and concentrated, and thus obtained product was crystallized in isopropanol to obtain 48.5 g of the product with a yield of 76%. MS(ESI) m/z 303.0([M+H]$^+$). The results were shown in table 1.

$^1$H NMR data of the compound of Formula IV prepared in the Examples 2 to 13 were the same as those of Example 1.

Comparative Example 1

Synthesis of 1-[2-fluoro-6-(trifluoromethyl) benzyl]-6-methylpyrimidin-2,4(1H,3H)-dione (Formula IV)

Compound of Formula II 1-[2-fluoro-6-(trifluoromethyl)] benzyl urea (2.568 g) and toluene (125 ml) were added to a 1 L flask and stirred for reflux, and then tert-butyl acetoacetate (5.0 g) was added thereto for reflux reaction for 4 h. P-toluenesulfonic acid monohydrate (2.82 g) was added to the reflux system to continue the reaction for 1 h. The obtained mixture was distilled to completely remove toluene, and then 30 ml of isopropanol was added thereto and stirred overnight. Thus obtained mixture was filtered, and the filter cake was washed with isopropanol to obtain the compound of Formula IV 1.81 g with a yield of 57%. MS(ESI) m/z 303.0([M+H]$^+$). The results were shown in table 1.

TABLE 1

Comparison of results obtained from different batches of examples

| Batch | Content of the compound of Formula IV (%) | Content of the compound of Formula IV-imp (%) | Yield (%) |
|---|---|---|---|
| Example 1 | 99.77% | 0.02% | 82% |
| Example 2 | 99.57% | 0.01% | 81% |
| Example 3 | 99.68% | 0.03% | 81% |
| Example 4 | 99.64% | 0.21% | 78% |
| Example 5 | 99.58% | 0.19% | 77% |
| Example 6 | 99.61% | 0.08% | 76% |
| Example 7 | 99.57% | 0.17% | 77% |
| Example 8 | 99.74% | 0.03% | 81% |
| Example 9 | 99.54% | 0.24% | 77% |
| Example 10 | 99.63% | 0.27% | 78% |
| Example 11 | 99.57% | 0.17% | 77% |
| Example 12 | 99.64% | 0.28% | 76% |
| Example 13 | 99.58% | 0.33% | 76% |
| Comparative Example 1 | 93.46% | 6.10% | 57% |

The method for preparing the intermediate of elagolix according to the present invention is described in connection with examples, and those skilled in the art can obviously realize the present invention by modifying or appropriately changing and combining with the method for preparing the intermediate of elagolix described herein without departing from the content, spirit and scope of the invention. In particular, it should be understood that all similar substitutions and changes will be obvious to those skilled in the art, and they are all considered to be included in the spirit, scope and content of the present invention.

The invention claimed is:

1. A method for preparing a compound of Formula IV, an intermediate of elagolix, comprising steps of: carrying out ammonolysis reaction of a compound of Formula I and a compound of Formula II in mixed solvent of organic solvent and water, and then carrying out cyclization reaction catalyzed by acid to obtain the compound of Formula IV;

wherein the volume ratio of the organic solvent to water is 1:0.001-2;

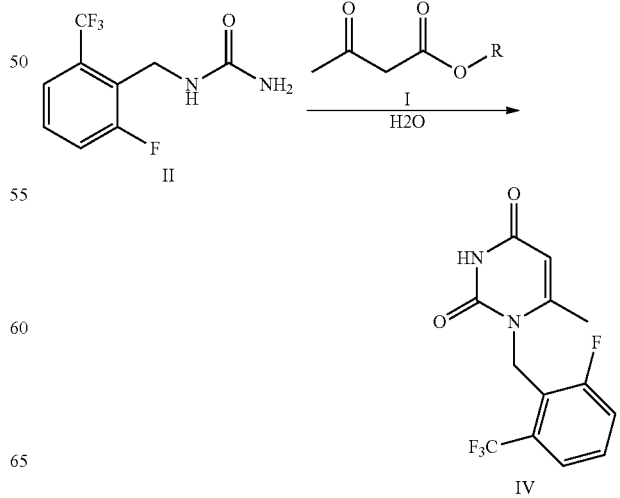

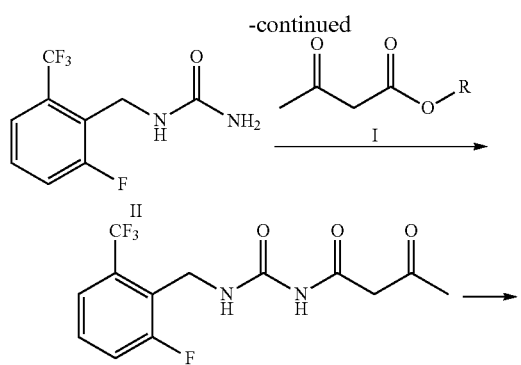

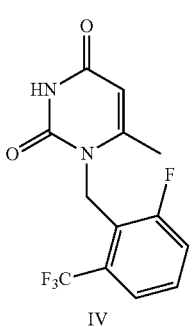

wherein R is selected from a group consisting of linear or branched $C_1$-$C_4$ substituent or benzyl.

2. The method according to claim 1, wherein the linear or branched $C_1$-$C_4$ substituents is selected from alkyl or alkenyl.

3. The method according to claim 1, wherein the organic solvent is an aprotic organic solvent.

4. The method according to claim 1, wherein the organic solvent is toluene.

5. The method according to claim 1, wherein the volume ratio of the organic solvent to water is 1:0.1-1.0.

6. The method according to claim 1, wherein the mass ratio of the compound of Formula I to the compound of Formula II is 1:0.66-4.

7. The method according to claim 1, wherein the ratio of the mass of the compound of Formula II to the volume of the mixed solvent is 1:8 to 1:20 with a unit of g/ml.

8. The method according to claim 1, wherein the reaction temperature of the ammonolysis reaction is 80° C. to 150° C.

9. The method according to claim 1, wherein the reaction temperature of the cyclization reaction catalyzed by the acid to prepare the compound of Formula IV is 40° C. to 150° C.

10. The method according to claim 1, wherein the acid is selected from a group consisting of p-toluenesulfonic acid, methanesulfonic acid, and sodium dihydrogen phosphate.

11. The method according to claim 1, wherein the mass ratio of the compound of Formula II to the acid is 1:0.5-1.5.

12. The method according to claim 2, wherein the alkyl is selected from a group consisting of methyl, ethyl, isopropyl and tert-butyl; and the alkenyl is selected from allyl.

13. The method according to claim 3, wherein the organic solvent is selected from a group consisting of toluene, chlorobenzene, xylene, N,N-dimethylformamide (DMF), dimethyl sulfoxide (DMSO) and combinations thereof.

14. The method according to claim 6, wherein the mass ratio of the compound of Formula I to the compound of Formula II is 1:1.5-2.0.

15. The method according to claim 8, wherein the reaction temperature of the ammonolysis reaction is 100° C. to 120° C.

16. The method according to claim 9, wherein the reaction temperature of the cyclization reaction catalyzed by the acid to prepare the compound of Formula IV is 60° C. to 120° C.

* * * * *